(12) United States Patent
Chassot et al.

(10) Patent No.: US 6,592,631 B2
(45) Date of Patent: Jul. 15, 2003

(54) P-AMINOPHENOL DERIVATIVE COMPOUNDS AND DYE COMPOSITIONS CONTAINING SAME

(75) Inventors: Laurent Chassot, Praroman (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 102 days.

(21) Appl. No.: 09/844,110

(22) Filed: Apr. 27, 2001

(65) Prior Publication Data

US 2001/0054207 A1 Dec. 27, 2001

(30) Foreign Application Priority Data

May 10, 2000 (DE) .......................... 100 22 829

(51) Int. Cl.$^7$ ................................. A61K 7/13
(52) U.S. Cl. ................... 8/405; 8/405; 8/409; 8/412; 8/421; 8/423; 548/400; 549/200; 549/1
(58) Field of Search ................... 8/405, 409, 412, 8/421, 423; 548/400; 549/200, 1

(56) References Cited

FOREIGN PATENT DOCUMENTS

| DE | 196 07 751 A1 | 9/1997 |
|----|---------------|--------|
| DE | 100 00 460 A1 | 8/2001 |
| WO | 01/51019 A1   | 7/2001 |

OTHER PUBLICATIONS

Anna Maria Almerico et al. Polycondensed Nitrogen Heterocycles. (J. Heterocyclic Chem., 31, 193 (1994).*
J. Heterocyclic Chem., 31 (1984), pp. 193–198.

* cited by examiner

Primary Examiner—Mark Kopec
Assistant Examiner—Eisa Elhilo
(74) Attorney, Agent, or Firm—Michael J. Striker

(57) ABSTRACT

The p-aminophenol derivative compounds of formula (I), or their physiologically compatible water-soluble salts:

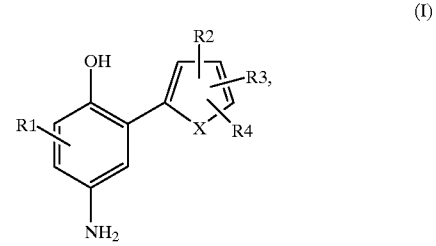

(I)

are useful as developer compounds in oxidation dye compositions for keratin fibers. Oxidation dye compositions for keratin fibers, including hair, and methods of dyeing hair using the p-aminophenol derivative compounds are also described.

16 Claims, No Drawings

P-AMINOPHENOL DERIVATIVE COMPOUNDS AND DYE COMPOSITIONS CONTAINING SAME

BACKGROUND OF THE INVENTION

1. Field of the Invention

The present invention relates to new p-aminophenol derivative compounds with substituents in the 2-position and compositions for dyeing keratin fibers, especially human hair, containing these new compounds.

2. Prior Art

Oxidation dye compounds have long attained substantial importance in the art of dyeing keratin fibers, especially hair dyeing. The dyeing caused by those compounds occurs by reaction of certain developer substances with certain coupler substances in the presence of a suitable oxidizing agent. For example, 2,5-diaminotoluene, 2,5-diaminophenylethyl alcohol, p-aminophenol and 1,4-diaminobenzene can be used as developer substances, while resorcinol, 4-chlororesorcinol, 1-naphthol, 3-aminophenol and derivatives of m-phenylen-diamine can be mentioned as coupler substances. There are numerous additional requirements for oxidation dye compounds that are used to dye human hair besides color in the desired intensity. Thus the dye compounds must be unobjectionable in regard to toxicological and dermatological properties and must provide the desired hair color with a good light fastness, fastness to a permanent wave treatment, acid fastness and fastness to rubbing. The color of the hair dyed with the dye compounds in each case must be stable for at least 4 to 6 weeks to light, rubbing and chemical agents. Furthermore an additional requirement is the production of a broad palette of different color shades using different developer and coupler substances. To obtain natural and especially fashionable color shades in the red region p-aminophenol is used, alone or in a mixture with another developer substance, in combination with a suitable coupler substance. Introduction of substituents on the p-aminophenol to improve its properties has already been attempted. DE-OS 196 07 751 discloses dye compositions, which contain p-aminophenol compounds with substituents in the 2-position acting as developer substances.

It is not possible to fulfill all the above-mentioned requirements with the currently known dye compounds. There is thus a need for new developer substances that fulfill the above-mentioned requirements in special ways.

SUMMARY OF THE INVENTION

It is an object of the present invention to provide improved developer compounds that fulfill the above-described requirements in a special manner.

It has now been surprisingly found that the new p-aminophenol derivative compounds according to formula (I) fulfill the many requirements for developer compounds to an especially great extent. Particularly bright or intense color shades are produced using these developer substances with predominantly known coupler substances, which are however extraordinarily light fast and fast to washing.

The subject matter of the present invention thus includes p-aminophenol derivative compounds of formula (I), or their physiologically compatible water-soluble salts,

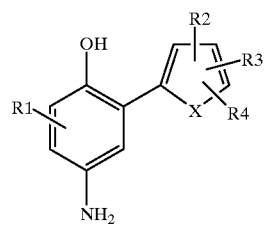

wherein
X is oxygen, sulfur or NR5,
R1 represents hydrogen, a halogen atom, a $C_1$- to $C_4$-alkyl group, a $C_1$- to $C_4$-hydroxyalkyl group or a $C_1$- to $C_4$-alkoxy group;
R2 and R4, independently of each other, each represent hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_6$-alkylamino group, a ($C_1$- to $C_6$)-dialkylamino group, a —C(O)H group, a —C(O)$CH_3$ group, a —C(O)$CF_3$ group, a —Si$(CH_3)_3$ group, a $C_1$- to $C_4$-hydroxyalkyl group, a $C_3$- to $C_4$-dihydroxyalkyl group, a —CH=CHR6 group, a —$(CH_2)_p$-$CO_2$R7 group or a —$(CH_2)_p$-R8 group, with p=1, 2, 3 or 4 a —C(R9)=NR10 group or a C(R11)H—NR12R13 group;
R3 represents hydrogen, a halogen atom, a $C_1$- to $C_6$-alkyl group, or a —C(O)H group;
R5 represents hydrogen, a $C_1$- to $C_6$-alkyl group, a $C_1$- to $C_4$-hydroxyalkyl group, a phenyl group or an acetyl group;
R6 represents hydrogen, a hydroxy group, a nitro group, an amino group, a —$CO_2$R7 group or a —C(O)$CH_3$ group;
R7, R9 and R11 each represent, independently of each other, hydrogen or a $C_1$- to $C_4$-alkyl group;
R8 represents an amino group or a nitrile group;
R10, R12 and R13 each represent, independently of each other, hydrogen, a hydroxy group, a $C_1$- to $C_4$-alkyl group, a $C_1$- to $C_4$-hydroxyalkyl group, a $C_3$- to $C_4$-dihydroxyalkyl group or a group of formula (II):

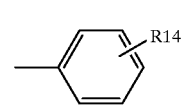

(II)

and R14 represents hydrogen, an amino group or a hydroxy group.

The compounds of formula (I) include especially: 4-amino-2-(2-thienyl)-phenol; 4-amino-2-(2-furyl)-phenol; 4-amino-2-(pyrrol-2-yl)-phenol; 4-amino-2-(1-methyl-1H-pyrrol-2-yl)phenol; 4-amino-3-chloro-2-(2-thienyl)-phenol; 4-amino-3-methyl-2-(2-thienyl)-phenol; 4-amino-5-chloro-2-(2-thienyl)phenol; 4-amino-5-methyl-2-(2-thienyl)phenol; 4-amino-6-chloro-2-(2-thienyl)-phenol; 4-amino-6-methyl-2-(2-thienyl)-phenol; 4-amino-2-(3-acetyl-2-thienyl)-phenol; 4-amino-2-(3-chloro-2-thienyl)-phenol; 4-amino-2-(3-formyl-2-thienyl)-phenol; 4-amino-2-(3-methyl-2-thienyl)-phenol; 4-amino-2-(3-nitro-2-thienyl)phenol; 4-amino-2-(4-acetyl-2-thienyl)-phenol; 4-amino-2-(4-chloro-2-thienyl)phenol; 4-amino-2-(4-formyl-2-thienyl)-phenol; 4-amino-2-(4-methyl-2-thienyl)phenol; 4-amino-2-(4-nitro-2-thienyl)phenol; 4-amino-2-(5-acetyl-2-thienyl)-phenol; 4-amino-2-(5-chloro-2-thienyl)-phenol;

4-amino-2-(5-formyl-2-thienyl)phenol; 4-amino-2-(5-methyl-2-thienyl)-phenol; 4-amino-2-(5-nitro-2-thienyl)phenol as well as physiologically compatible salts of these compounds.

Preferred compounds of formula (I) include those in which (i) R1 represents hydrogen and/or (ii) at least one of the groups R2, R3 and R4 represents hydrogen or a methyl group and/or (iii) X represents sulfur or oxygen.

The particularly preferred p-aminophenol derivative compounds of formula (I) include 4-amino-2-(2-thienyl)phenol; 4-amino-2-(3-methyl-2-thienyl) phenol and 4-amino-2-(5-methyl-2-thienyl) phenol and its physiologically compatible derivative compounds.

The compounds of formula (I) can be employed both as free bases and also in the form of their physiologically compatible salts with inorganic or organic acids, such as hydrochloroic acid, sulfuric acid, phosphoric acid, acetic acid, propionic acid, lactic acid or citric acid.

The preparation of aminophenol derivative compounds of formula (I) can occur using the known literature synthesis methods. For example, it can occur by a palladium (0) catalyzed coupling of a substituted benzene of formula (II):

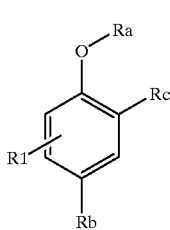

(II)

with a heterocyclic compound of the formula (III):

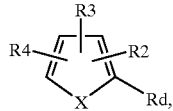

(III)

subsequently splitting off the protective group and, if necessary, reducing the nitro group; wherein the groups in formula (II) and (III) have the following significance: Ra represents a protective group, for example as described in the chapter "Protective Groups" in Organic Synthesis, Chapter 7, Wiley Interscience, 1991 and Rb represents NHRa group or a nitrogroup; one of the groups Rc and Rd represent a halogen group, while the other represents a B(OH) group, and X, R1, R2, R3 and R4 have the same significance as in formula (I).

The compounds of formula (I) are especially suitable as developer substances in oxidation dye compositions and permit a broad palette of various color shades, which extend from blonds to browns, purples, violets to blue and black shades.

Oxidation dye compositions for oxidative dyeing of keratin fibers, for example hair, fur, feathers or wool, especially human hair, based on a combination of developer and coupler substances, which contain at least one p-aminophenol derivative compound of formula (I) as developer substance, are also part of the subject matter of the present invention.

The aminophenol derivative compounds of formula (I) are present in the oxidation dye compositions according to the invention in an amount of about 0.005 to 20 percent by weight, however an amount of from about 0.01 to 5.0 percent by weight is preferred and an amount of from 0.1 to 2.5 percent by weight is particularly preferred.

The following coupler compounds are preferred in the compositions according to the invention: 2,6-diaminopyridine, 2-amino-4-[(2-hydroxyethyl)-amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxy-benzene, 2,3-diamino-6-methoxypyridine, 3-amino-6-methoxy-2-(methylamino)-pyridine, 2,6-diamino-3, 5-dimethoxy-pyridine, 3,5-diamino-2,6-dimethoxy-pyridine, 1,3-diaminobenzene, 2,4-diamino-1-(2-hydroxyethoxy)benzene, 2,4-diamino-1,5-di(2-hydroxyethoxy)benzene, 1-(2-aminoethoxy)-2,4-diamino-benzene, 2-amino-1-(2-hydroxyethoxy)-4-methylaminobenzene, 2,4-diamino-phenoxyacetic acid, 3-[di(2-hydroxyethyl)amino]aniline, 4-amino-2-di[(2-hydroxy-ethyl)amino]-1-ethoxybenzene, 5-methyl-2-(1-methylethyl)phenol, 3-[(2-hydroxy-ethyl)amino]aniline, 3-[(2-aminoethyl)amino]aniline, 1,3-di(2,4-diaminophenoxy)-propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)-amino]acetamide, 5-[(2-hydroxyethyl)amino]-2methylphenol, 3-[(2-hydroxyethyl)-amino]phenol, 3-[(2-methoxyethyl)amino]phenol, 5-amino-2-ethylphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-Hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1 3-dihydroxy-2-methylbenzene, 3,4-methylendioxyphenol, 3,4-methylendioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4-(2H)-benzoxazine, 6-amino-3,4-dihydroxy-1,4(2H)-benzoxazine, 3-methyl-1-phenyl-5-pyrazolone, 5,6-dihydroxyindole, 5,6-dihydroxyindolene, 5-hydroxyindole, 6-hydroxyindole, 7-hydroxyindole and 2,3-indolindione.

Although the advantageous properties of the aminophenol derivative compounds of formula (I) described here obviously will be obtained if they are used as sole developer substance, it is advantageously also possible to use the aminophenol derivative compounds of formula (I) together with known developer substances, such as 1,4-diaminobenzene, 2,4-diaminotoluene, 2,5-diaminophenylethyl alcohol, N,N-bis-(2'-hydroxyethyl)-1,4-diaminobenzene, 4-aminophenol and its derivative compounds, for example 4-amino-3-methyl-phenol, 4,5-diamino-1-(2-hydroxyethyl)pyrazole or tetraaminopyrimidenes.

The coupler substances and developer substances can be contained in the dye compositions according to the invention, individually or together in a mixture. The total amount of coupler and developer substances in the dye compositions of the invention (based on the total amount of the dye composition) amounts to about 0.005 to 20 percent by weight respectively, preferably about 0.01 to 5.0 percent by weight each and especially preferably from 0.1 to 2.5 percent by weight each.

The total amount of the combination of developer and coupler substances in the dye composition according to the invention preferably amounts to from about 0.01 to 20 percent by weight, but an amount of from about 0.02 to 10 percent by weight is preferred and an amount of from about 0.2 to 6.0 percent by weight is especially preferred. The developer and coupler substances are generally used in about equimolar amounts, however it is not disadvantageous when the developer substance is present in a lesser or greater amount than an equimolar amount with respect to the coupler substance.

The dye composition according to the invention can also contain other dye compounds, for example 6-amino-2-methylphenol and 2-amino-5-methylphenol, and direct-dyeing dye compounds, for example triphenylmethane dye compounds, such as 4-[(4'-aminophenyl)-(4'-imino-2",5"-cyclohexadien-1"-yliden)-methyl]-2-methylaminobenzene monohydrochloride (C.I. 42 510) and 4-[(4'-amino-3'-methylphenyl)-(4"-imino-3"-methyl-2",5"-cyclohexadien-1"-2-methylamino-benzene monohydrochloride (C.I. 42 520); aromatic nitro dye compounds, such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)4-nitrophenol, 4-chloro-N-(2-hydroxyethyl)-2-nitroaniline, 5-chloro-2-hydroxy-4-nitroaniline, 2-amino-4-chloro-6-nitro-phenol and 1-[(2'-ureidoethyl)-amino-4-nitrobenzene; azo dye compounds, such as 6-[(4'-amino-phenyl)azo]-5-hydroxynapthhalen-1-sulfonic acid sodium salt (C.I. 14 805) and dispersion dye compounds, such as 1,4-diaminoanthraquinone and 1,4,5,8-tetraamino-anthraquinone and cationic dye compounds. These dye compounds can be contained in the dye composition of the invention in an amount of from about 0.1 to 4.0 percent by weight.

Understandably the coupler substances and the developer substances as well as the other dye compounds, in so far as they are bases, can also be used in the form of their physiologically compatible salts with organic or inorganic acids, such as hydrochloric acid or sulfuric acid, or, in so far as they have aromatic OH groups, in the form of their salts with bases, such as alkali phenolates.

Moreover cosmetic additive ingredients, which are commonly used in compositions for dyeing hair, can be used in the dye compositions according to the invention, for example antioxidants, such as ascorbic acid, thioglycolic acid or sodium sulfite, and perfume oils, complex formers, wetting agents, emulsifiers, thickeners and care materials.

The form of the dye compositions according to the invention can be, for example, a solution, especially an aqueous or aqueous-alcoholic solution. However the forms that are particularly preferred are a cream, gel and an emulsion. Its composition is a mixture of the dye ingredients with the conventional cosmetic additive ingredients suitable for the particular preparation.

Conventional cosmetic additive ingredients in solutions, creams, emulsion or gels include, for example, solvents, such as water, lower aliphatic alcohols, such as ethanol, propanol or isopropanol, glycerol or glycols, such as 1,2-propylene glycol, wetting agents or emulsifiers from the classes of anionic, cationic, amphoteric or nonionic surfactant compounds, such as fatty alcohol sulfates, ethoxylated fatty alcohol sulfates, alkylsulfonates, alkylbenzene-sulfonates, alkyltrimethylammonium salts, alkylbetaines, ethoxylated fatty alcohols, ethoxylated nonylphenols, fatty acid alkanol amides and ethoxylated fatty acid esters; thickeners, such as higher fatty alcohols, starches, cellulose derivatives, petrolatum, paraffin oil and fatty acids, as well as care materials, such as cationic resins, lanolin derivatives, cholesterol, pantothenic acid and betaine. The above-mentioned conventional cosmetic ingredients are used in amounts suitable for their purposes. For example, the wetting agents and emulsifiers are used in concentrations of from about 0.5 to 30 percent by weight, the thickeners are used in an amount of from about 0.1 to 25 percent by weight and the care materials are used in concentrations of from about 0.1 to 5.0 percent by weight.

The dye compositions according to the invention can be weakly acidic, neutral or alkaline according to their composition. The compositions preferably have a pH from 6.5 to 11.5. Their pH can be adjusted in the basic range with ammonia. Also organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair dye composition for dyeing hair the above-described dye compositions according to the invention are mixed with an oxidizing agent immediately prior to use and an amount of the mixture sufficient to dye the hair is applied to the hair, according to the hair abundance, generally from about 60 to 200 grams.

Principally hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Air oxygen can also be used as the oxidizing agent. If a 6 percent hydrogen peroxide solution is used as oxidizing agent, the weight ratio of hair dye composition and oxidizing agent is 5:1 to 1:2, but preferably 1:1. Larger amounts of oxidizing agent are used above all with larger dye concentrations in the hair dye composition, or when at the same time a strong bleaching of the hair is desired. The mixture of the oxidizing agent and the dye composition of the invention is allowed to act on the hair for about 10 to 45 minutes, preferably 30 minutes, at 15 to 50 degrees Celsius. The hair is then rinsed with water and dried. If necessary it is washed with a shampoo and eventually after-rinsed with a weak organic acid, such as citric acid or tartaric acid. Subsequently the hair is dried.

The hair dye composition according to the invention with a content of diaminobenzene derivative compounds of formula (I) as developer substance permits hair dyeing with outstanding color fastness, especially light fastness, fastness to washing and fastness to rubbing. The dye composition according to the invention provides a broad palette of different color shades, which extend from blond to brown, purple, violet to blue and black shades, according to the type and composition of the dye compounds in it. Particularly the color shades produced have outstanding color intensity. The very good dyeing properties of the compositions according to the invention include the production of good color coverage and dyeing of gray, chemically not-previously damaged hair without problems.

The following examples should serve to illustrate the invention, but details present in these examples should not

EXAMPLES

Example 1

Synthesis of 4-amino-2-(2-thienyl)phenol

A. Synthesis of 2-bromo-4-nitrophenol 2-bromo-4-nitrophenol is prepared by reaction of 4-nitrophenol with N-brom-succinimide, according to the paper by T. Oberhouser in J. Org. Chem. 62, pp. 4504 and following (1997).

B. Synthesis of 2-bromo-1-methoxymethoxy-4-nitrobenzene 4.2 g (140 mmol) of a sodium hydride dispersion (55% in oil) are added portion-wise at 0° C. to a solution of 15.3 g 2-bromo-4-nitrophenol (70 mmol) in 250 ml tetrahydrofuran. Subsequently the reaction mixture is stirred for 50 minutes at 0° C. and then mixed with 1.83 g of chloromethyl-methyl ether (19.4 mmol). The mixture is stirred for an additional hour at 0° C. and then poured into ice, extracted with ethyl acetate and the organic phase is washed with a saturated aqueous salt solution, dried over $Na_2SO_4$, filtered and concentrated. The residue so obtained is concentrated over silica gel with petroleum ether/ethyl acetate (9:1). 15.8 g (80% theoretical yield) of 2-bromo-1-methoxymethoxy-4-nitrobenzene are obtained.

$^1$H-NMR (300 MHz, $CDCl_3$): δ=8.48 (s, 1H); 7.08(d, 1H); 8.16 (d; 1H); 7.26 (d, 1 H); 5.36 (s, 2H); 3.53 (s, 3H)

C. Synthesis of 4-Nitro-2-(2-thienyl)phenol 5.3 g (20 mmol) 2-bromo-1-methoxymethoxy-4-nitrobenzene and 2.95 9 (23 mmol)-2-thienylboric acid are dissolved in 70 ml of 1,2-dimethoxyethane under argon. Subsequently 0.5 g (0.5 mmol) tetrakis-(triphenylphosphin) palladium and 13 ml of a 2 Normal potassium carbonate solution are added and the reaction mixture is heated to 80° C. After terminating the reaction the reaction mixture is poured into 100 ml of ethyl acetate, the organic phase is extracted with dilute sodium hydroxide solution and then dried with magnesium sulfate. The solvent is distilled off in a rotary evaporator and the residue is purified on silica gel with petroleum ether/ethyl acetate(9:1). The product so obtained is heated in a mixture of 40 ml ethanol and 15 ml of a 2.9 molar ethanolic hydrochloric acid solution to 50° C. After neutralization with sodium hydroxide the solvent is distilled off in a rotary evaporator and the residue is purified by vacuum distillation.

4.0 g (83% of theoretical yield) of 4-nitro-2-(2-thienyl) phenol are obtained having a melting point of 130° C.

D. Synthesis of 4-amino-2-(2-thienyl)phenol 3 g (13.5 mmol) of 4-nitro-2-(2-thienyl)phenol are dissolved in 40 ml ethanol and hydrogenated at 25° C. after addition of 600 mg of a palladium activated carbon catalyst (10%). The catalyst is removed by filtration after up-take of the theoretically required amount of hydrogen. After concentrating the solution in a rotary evaporator the reaction mixture is poured into 20 ml of cold diethyl ether. The precipitated product is separated from the solution by filtration and dried. 1.95 g (75% of theoretical yield) of 4-amino-2-(2-thienyl)phenol are obtained with a melting point of 130 to 132° C.

CHN Analysis

| ($C_{10}H_9NOS$) | % C | % H | % N |
| --- | --- | --- | --- |
| Calculated: | 62.80 | 4.74 | 7.32 |
| Found: | 62.45 | 4.88 | 6.83 |

Example 2

Synthesis of 4-amino-2-(2-heteroaryl)phenol derivative compounds of formula (I) (General Preparation Method)

A. Synthesis of N-(3-bromo4-hydroxyphenyl) carbamic acid tert.-butyl ester

A solution of 9.4 g of N-bromsuccinimide (52.8 mmol) in 450 ml chloroform is added dropwise to a suspension of N-(4-hydroxyphenyl)carbamic acid tert.-butyl ester (10 g, 47.8 mmol) in 100 ml of chloroform within 2 hours at 0° C. The reaction mixture is subsequently stirred an additional 15 minutes, then washed twice with water (first 400 ml, then 200 ml), dried with magnesium sulfate, filtered and partially concentrated. The residue is then mixed with hexane while being stirred so that a precipitate forms. The precipitate is filtered off and washed with hexane.

9.7 g (70% of theoretical yield) of N-(3-bromo-4-hydroxyphenyl)carbamic acid tert.-butyl ester are obtained.

$^1$H-NMR (300 MHz, $CDCl_3$): δ=7.68 (br s, 1H); 7.05 (dd, 1 H); 6.93 (d; 1H); 6.37 (br s, 2H), 5.39 (s, 1 H); 1.51 (s, 9H)

B. Synthesis of N-(3-bromo-4-ethoxymethoxyphenyl)carbamic acid-tert.-butyl ester 0.76 g (17.4 mmol) of a sodium hydride dispersion (55% in oil) are added portion-wise to a solution of 5 g of N-(3-bromo-4-hydroxyphenyl)carbamic acid tert.-butyl ester (17.4 mmol) in 60 ml tetrahydrofuran. Subsequently the reaction mixture is stirred for 50 minutes at 0° C. and then mixed with 1.83 g of chloromethyl-methyl ether (19.4 mmol). The mixture is stirred for an additional hour at 0° C. and then poured into ice, extracted with ethyl acetate and the organic phase is washed with a saturated aqueous salt solution, dried over $Na_2SO_4$, filtered and concentrated. The residue so obtained is concentrated over silica gel with petroleum ether/ethyl acetate (9:1).

4.8 g (80% theoretical yield) of N-(3-bromo-4-ethoxymethoxyphenyl)carbamic acid-tert.-butyl ester are obtained.

$^1$H-NMR (300 MHz, $CDCl_3$): δ=7.66 (d, 1H); 7.16 (dd, 1H); 7.08 (d; 1H); 5.23 (s, 2H); 3.77 (q, 2H); 1.51 (s, 9H); 1.22 (t, 3H)

C. Synthesis of N-[4-ethoxymethoxy-3-(4,4,5,5-tetramethyl[1,3,2]dioxaborolan-2-yl)phenyl] carbamic acid-tert.butyl ester A mixture of 7.0 g (20.2 mmol) N-(3-bromo-4-ethoxymethoxyphenyl)carbamic acid tert.butyl ester, 12.8 g (50.6 mmol) diboronpinacol ester, 2.0 g (2.9 mmol) dichloro (1,1'-bis(diphenylphosphino)ferrocene)palladium ($PdCl_2$ (dppf)) and 6.2 g (63.2 mmol) of potassium acetate are mixed under argon with 210 ml of degassed dioxan. The mixture is subsequently stirred for 26 hours at 80° C. and then mixed with a mixture of 4.2 g (16.9 mmol) diboronpinacol ester and 0.7 g (0.95 mmol) PdCl$_2$ (dppf) and stirred again for 14 hours at 80° C. Subsequently the reaction mixture is poured into water, extracted with ethyl acetate and the organic phase is washed with a saturated aqueous salt solution, dried over Na$_2$SO$_4$ and concentrated after filtration. The crude product is subsequently purified on deactivated silica gel with hexane/ethyl acetate. 5.30 g (61% of theoretical yield) of N-[4-ethoxymethoxy-3-(4,4,5,5-tetramethyl[1,3,2]dioxaborolan-2-yl)phenyl]carbamic acid-tert. butyl ester were obtained.

D. Synthesis of 4-amino-2-(2-heteroaryl)phenols 0.036 g (0.1 mmol) N-[4-ethoxymethoxy-3-(4,4,5,5-tetramethyl[1,3,2]-dioxaborolan-2-yl)phenyl]carbamic acid-tert.butyl ester and 0.013 of the corresponding bromo derivative are dissolved in 70 ml of 1,2-dimethoxyethane under argon. Subsequently 0.5 g (0.5 mmol) tetrakis-(triphenylphosphin)-palladium and 13 ml of a 2 Normal potassium carbonate solution are added and the reaction mixture is heated to 80° C. After terminating the reaction, the reaction mixture is poured into 100 ml ethyl acetate, the organic phase is extracted with dilute sodium hydroxide solution and then dried with magnesium sulfate. The solvent is distilled off in a rotary evaporator and the residue is purified on silica gel with petroleum ether/ethyl acetate (9:1). The product so obtained is heated in a mixture of 40 ml ethanol at 50° C. Then 15 ml of a 2.9 molar ethanolic hydrochloric acid solution are added dropwise. The precipitate is filtered off, washed twice with 10 ml ethanol and dried.

a. 4-amino-2-(5-methylthiophen-2-yl)phenol hydrochloride
   Bromo derivative compound: 2-bromo-5-methylthiophene
   Yield: 0.025 g (98% theoretical yield) Mass spectrum: MH$^+$206(100)
b. 4-amino-2-(5-nitrothiophen-2-yl)phenol hydrochloride
   Bromo derivative compound: 2-bromo-5-nitrothiophene
   Yield: 0.025 g (93% theoretical yield) Mass spectrum: MH$^+$237(85)
c. 4-amino-2-furan-2-yl-phenol hydrochloride
   Bromo derivative compound: 2-bromofuran
   Yield: 0.012 g (53% theoretical yield) Mass spectrum: MH$^+$176(100)

Examples 3 to 18

Hair Dye Compositions

Hair dye solutions of the following compositions were prepared:

| | | |
|---|---|---|
| 1.25 mmol | Developer substance of formula I according to Table 1 | |
| 1.25 mmol | Coupler substance according to Table I | |
| 1.0 g | Potassium oleate (8 percent aqueous solution) | |
| 1.0 g | Ammonia (22% aqueous solution) | |
| 1.0 g | Ethanol | |
| 0.3 g | Ascorbic acid | |
| to 100.0 g | Water | |

30 g of the above-described dye solution are mixed with 30 g of a 6 percent aqueous hydrogen peroxide solution immediately prior to application on the hair. Subsequently the mixture is applied to bleached hair. After an acting time of 30 minutes at 40° C. the hair is rinsed with water, washed with a commercial shampoo and dried. The resulting dyed hair colors are tabulated in the following Table I:

TABLE 1

DYED HAIR COLORS OBTAINED WITH THE HAIR DYE COMPOSITIONS OF EXAMPLES 3 TO 18

| Example/ Color Shade | Developer Substance Of formula (I) | Coupler Substance |
|---|---|---|
| 3 Bright blond | 4-amino-2-(2-thienyl)-phenol | 1,3-dihydroxybenzene |
| 4 bright blond | 4-amino-2-(5-methyl-thiophen-2-yl)phenol hydrochloride | 1,3-dihydroxybenzene |
| 5 bright blond | 4-amino-2-(5-nitro-thiophen-2-yl)phenol hydrochloride | 1,3-dihydroxybenzene |
| 6 bright blond | 4-amino-2-furan-2-yl-phenol hydrochloride | 1,3-dihydroxybenzene |
| 7 red-violet | 4-amino-2-(2-thienyl)-phenol | 1,3-diamino-4-(2'-hydroxyethoxy)benzene sulfate |
| 8 red-violet | 4-amino-2-(5-methyl-thiophen-2-yl)phenol hydrochloride | 1,3-diamino-4-(2'-hydroxyethoxy)benzene sulfate |
| 9 brown | 4-amino-2-(5-nitro-thiophen-2-yl)phenol hydrochloride | 1,3-diamino-4-(2'-hydroxyethoxy)benzene sulfate |
| 10 brown | 4-amino-2-furan-2-yl-phenol hydrochloride | 1,3-diamino-4-(2'-hydroxyethoxy)benzene sulfate |
| 11 red-orange | 4-amino-2-(2-thienyl)-phenol | 5-amino-2-methylphenol |
| 12 red-orange | 4-amino-2-(5-methyl-thiophen-2-yl)phenol hydrochloride | 5-amino-2-methylphenol |
| 13 brown | 4-amino-2-(5-nitro-thiophen-2-yl)phenol hydrochloride | 5-amino-2-methylphenol |
| 14 brown | 4-amino-2-furan-2-yl-phenol hydrochloride | 5-amino-2-methylphenol |
| 15 violet | 4-amino-2-(2-thienyl)-phenol | 1-naphthol |
| 16 violet | 4-amino-2-(5-nitro-thiophen-2-yl)phenol hydrochloride | 1-naphthol |
| 17 copper color | 4-amino-2-(5-nitro-thiophen-2-yl)phenol hydrochloride | 1-naphthol |
| 18 copper color | 4-amino-2-furan-2-yl-phenol hydrochloride | 1-naphthol |

Examples 19 to 34

Hair Dye Compositions

Hair dye solutions of the following compositions were prepared:

| | | |
|---|---|---|
| X g | Developer substance E1 of formula (I) according to Table III | |
| U g | Developer substance E2 to E 9 according to Table III | |
| Y g | Coupler substance K11 to K36 according to Table IV | |
| Z g | direct-dyeing dye compound D1 to D3 of Table II | |
| 10.0 g | Potassium oleate (8 percent aqueous solution) | |
| 10.0 g | Ammonia (22% aqueous solution) | |
| 10.0 g | Ethanol | |
| 0.3 g | Ascorbic acid | |
| to 100.0 g | Water | |

30 g of the above-described dye solution are mixed with 30 g of a 6 percent aqueous hydrogen peroxide solution immediately prior to application on the hair. Subsequently the mixture is applied to bleached hair. After an acting time of 30 minutes at 40° C. the hair is rinsed with water, washed with a commercial shampoo and dried. The resulting dyed hair colors and amounts X, Y, U and G are tabulated in the following Table V for the various dye compositions.

Examples 35 to 40

Hair Dye Compositions

Hair dye solutions of the following compositions were prepared:

| | |
|---|---|
| X g | Developer substance E1 of formula (I) according to Table III |
| Y g | Coupler substance K11 to K36 according to Table IV |
| Z g | direct-dyeing dye compound D1 to D3 of Table II |
| 15.0 g | cetyl alcohol |
| 0.3 g | ascorbic acid |
| 3.5 g | sodium lauryl alcohol diglycol ether sulfate, 28% aqueous solution |
| 3.0 g | Ammonia (22% aqueous solution) |
| 0.3 g | Sodium sulfite, water-free |
| to 100.0 g | Water |

30 g of the above-described dye solution are mixed with 30 g of a 6 percent aqueous hydrogen peroxide solution immediately prior to application on the hair. Subsequently the mixture is applied to bleached hair. After an acting time of 30 minutes the hair is rinsed with water, washed with a commercial shampoo and dried. The resulting dyed hair colors and amounts X, Y and G are tabulated in the following Table VI for the various dye compositions.

TABLE II

DIRECT-DYEING DYE COMPOUNDS

| | |
|---|---|
| D1 | 2,6-diamino-3-((pyridin-3-yl)azo)pyridine |
| D2 | 6-chloro-2-ethylamino-4-nitrophenol |
| D3 | 2-amino-6-chloro-4-nitrophenol |

TABLE III

DEVELOPER SUBSTANCES

| | |
|---|---|
| E1 | 4-amino-2-(2-thienyl)phenol (according to example 1D) |
| E2 | 1,4-diaminobenzene |
| E3 | 2,5-diaminophenylethanol sulfate |
| E4 | 3-methyl-4-aminophenol |
| E5 | 4-amino-2-aminomethylphenol dihydrochloride |
| E6 | 4-aminophenol |
| E7 | N,N-bis(2'-hydroxyethyl)-phenylenediamine sulfate |
| E8 | 4.5-diamino-1-(2'-hydorxyethyl)pyrazole sulfate |
| E9 | 2,5-diaminotoluene sulfate |

TABLE IV

COUPLER SUBSTANCES

| | |
|---|---|
| K11 | 1,3-diaminobenzene |
| K12 | 2-amino-4-(2'-hydroxyethyl)aminoanisole sulfate |
| K13 | 1,3-diamino-4-(2'-hydroxyethoxy)benzene sulfate |
| K14 | 2,4-diamino-5-fluorotoluene sulfate |
| K15 | 3-amino-2-methylamino-6-methoxypyridine |
| K16 | 3,5-diamino-2,6-dimethoxypyridine dihydrochloride |
| K17 | 2,4-diamino-5-ethoxytoluene sulfate |
| K18 | N-(3-dimethylamino)phenylurea |
| K19 | 1,3-bis(2,4-diaminophenoxy)propane tetrahydrochloride |
| K21 | 3-aminophenol |
| K22 | 5-amino-2-methylphenol |

TABLE IV-continued

COUPLER SUBSTANCES

| | |
|---|---|
| K23 | 3-amino-2-chloro-6-methylphenol |
| K24 | 5-amino-4-fluoro-2-methylphenol sulfate |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |
| K34 | 4-(2'-hydroxyethyl)amino-1,2-methylendioxybenzene Hydrochloride |
| K35 | 3,4-methylendioxyphenol |
| K36 | 2-amino-5-methylphenol |

TABLE V

HAIR DYE COMPOSITIONS OF THE INVENTION AND DYED HAIR COLORS

| Example/Ingredient/Color | 19 | 20 | 21 | 22 | 23 | 24 |
|---|---|---|---|---|---|---|
| E1 | 0.096 | 0.24 | 0.3 | 0.04 | 0.01 | 0.7 |
| E2 | | | | 0.9 | | |
| E5 | | | | | | |
| E6 | | | | | | |
| E9 | | | | | 0.096 | 1.8 |
| K12 | | | | | 0.01 | |
| K18 | | | | | | 0.03 |
| K21 | | | | | 0.02 | 0.06 |
| K22 | 0.08 | 0.2 | 0.25 | 0.056 | | 0.58 |
| K25 | | | | | 0.03 | |
| K31 | | | | 0.2 | | 0.8 |
| K32 | | 0.03 | 0.05 | 0.316 | | |
| K35 | 0.018 | | | | | |
| K36 | | 0.03 | 0.05 | 0.01 | | |
| K26 | | | | | | |
| D1 | | | | | 0.01 | |
| D3 | 0.04 | 0.06 | 0.025 | | | |
| Color | Bright blond/Copper gold | Copper-gold | Bright Copper color | Purple-brown | Silver blond | Dark Mahogany |

| Example/Ingredient | 25 | 26 | 27 | 28 | 29 | 30 |
|---|---|---|---|---|---|---|
| E1 | 0.01 | 0.6 | 1 | 0.2 | 0.8 | 0.6 |
| E2 | 2.0 | | | 1.9 | | |
| E3 | | 0.05 | | | | |
| E8 | | | 1 | | | |
| E9 | | | | | 1 | 0.7 |
| K12 | | | 1.1 | | | |
| K13 | 0.07 | | | | | 0.8 |
| K16 | | | | | | 1.0 |
| K17 | | | 1.1 | | | |
| K18 | | | | 1.25 | | |
| K21 | 0.4 | | | 0.28 | | |
| K22 | 0.08 | 0.5 | | | | |
| K25 | | | | | 0.8 | |
| K31 | 0.8 | | | | | |
| K32 | | 0.03 | | | | |
| K33 | | | | | 0.75 | |
| K36 | | 0.03 | | | | |
| D1 | | 0.25 | | | | |
| D3 | | 0.15 | | | | |
| Color | Black-brown | Orange | Blue-Violet | Blue-red | Pink | Bordeaux |

| Example/Ingredient/ | 31 | 32 | 33 | 34 |
|---|---|---|---|---|
| E1 | 0.01 | 0.01 | 0.05 | 0.6 |
| E3 | 1.4 | 4.5 | | |
| E5 | | | 0.25 | |

TABLE V-continued

HAIR DYE COMPOSITIONS OF THE INVENTION AND DYED HAIR COLORS

| | | | | |
|---|---|---|---|---|
| E6 | | 0.1 | | |
| E8 | 0.8 | 0.5 | 0.01 | |
| E9 | 2.5 | | | |
| K12 | 0.6 | | | |
| K13 | 0.2 | | 0.8 | |
| K14 | | 0.25 | | |
| K16 | 0.01 | | | |
| K18 | | | 1.25 | |
| K19 | 0.8 | | | |
| K21 | 0.3 | | 0.28 | |
| K22 | | 5.0 | | |
| K25 | | 0.4 | | |
| K23 | | | 0.6 | |
| K31 | 1.1 | | | |
| K32 | | | 0.33 | |
| K36 | | 0.19 | | |
| D2 | | | 0.5 | |
| Color | Black | Red-Violet | Red-Orange | Warm Yellow |

(amounts in Table V are in grams)
(amounts of the ingredients in Table V are in grams)

TABLE VI

HAIR DYE COMPOSITIONS OF THE INVENTION AND DYED HAIR COLORS

| Example/Ingredient/Color | 35 | 36 | 37 | 38 | 39 | 40 |
|---|---|---|---|---|---|---|
| E1 | 0.1 | 0.2 | 0.01 | 2.0 | 0.5 | 0.7 |
| E4 | | | | | | 1.6 |
| E8 | | | 0.25 | | 0.8 | 0.2 |
| E9 | 3.2 | 1.71 | 0.02 | | | 1.8 |
| K13 | 0.23 | 0.1 | | | 1.3 | |
| K14 | 0.2 | | | | | |
| K16 | | | 0.015 | | | |
| K21 | 0.4 | 0.8 | | | 0.02 | |
| K22 | 0.08 | | 0.25 | 1.8 | | 4.5 |
| K23 | | 0.2 | | | 0.03 | |
| K31 | 1.05 | 0.135 | 0.02 | 0.25 | | 0.8 |
| K25 | | | | | | 0.55 |
| K26 | | | 0.03 | | | |
| K19 | | | | | 1.7 | |
| K36 | | 0.27 | | | | |
| D2 | | 0.01 | | | | |
| Color | Dark brown | Chocolate Brown | Silver blond | Orange | Blue Violet | Red violet |

(amounts in Table VI are in grams)

All percentages, unless otherwise indicated, are percentages by weight.

The disclosure in German Patent Application 100 22 829.1 of May 10, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in p-aminophenol derivative compounds and dye compositions containing same, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A p-aminophenol derivative compound of formula (I), or a physiologically compatible water-soluble salt thereof,

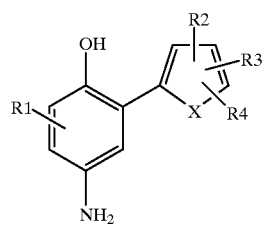

(I)

wherein X is oxygen or sulfur,

R1 represents hydrogen, a halogen atom, a $C_1$- to $C_4$-alkyl group, a $C_1$- to $C_4$-hydroxyalkyl group or a $C_1$- to $C_4$-alkoxy group;

R2 and R4, independently of each other, each represent hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_6$-alkylamino group, a ($C_1$- to $C_6$)-dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR6 group, a —(CH$_2$)$_p$—CO$_2$R7 group or a —(CH$_2$)$_p$—R8 group, with p=1, 2, 3 or 4, a —C(R9)=NR10 group or a C(R11)H—NR12R13 group;

R3 represents -hydrogen, a halogen atom, a $C_1$- to $C_6$-alkyl group, or a —C(O)H group;

R6 represents hydrogen, a hydroxy group, a nitro group, an amino group, a —CO$_2$R7 group or a —C(O)CH$_3$ group;

R7, R9 and R11 each represent, independently of each other, hydrogen or a $C_1$- to $C_4$-alkyl group;

R8 represents an amino group or a nitrile group;

R10, R12 and R13 each represent, independently of each other, hydrogen, a hydroxy group, a $C_1$- to $C_4$-alkyl group, a $C_1$- to $C_4$-hydroxyalkyl group, a $C_3$- to $C_4$-dihydroxyalkyl group or a group of formula (II):

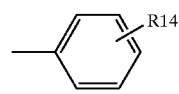

(II)

and R14 represents hydrogen, an amino group or a hydroxy group.

2. A p-aminophenol derivative compound, or a physiologically compatible salt thereof, said p-aminophenol derivative compound being selected from the group consisting of 4-amino-2-(2-thienyl)-phenol; 4-amino-2-(2-furyl)-phenol; 4-amino-3-chloro-2-(2-thienyl)-phenol; 4-amino-3-methyl-2-(2-thienyl)-phenol; 4-amino-5-chloro-2-(2-thienyl)phenol; 4-amino-6-methyl-2-(2-thienyl)-phenol; 4-amino-6-chloro-2-(2-thienyl)-phenol; 4-amino-6-methyl- 2-(2-thienyl)-phenol; 4-amino-2-(3-acetyl-2-thienyl)-phenol; 4-amino-2-(3-chloro-2-thienyl)-phenol; 4-amino-2-(3-formyl-2-thienyl)-phenol; 4-amino-2(3-methyl-2-thienyl)-phenol; 4-amino-2-(3-nitro-2-thienyl)phenol; 4-amino-2-(4-acetyl-2-thienyl)-phenol; 4-amino-2-(4-chloro-2-thienyl)phenol; 4-amino-2-(4-formyl-2-thienyl)-phenol; 4-amino-2-(4-methyl-2-thienyl)phenol; 4-amino-2-(4-nitro-2-thienyl)phenol; 4-amino-2-(5-acetyl-2-thienyl)-phenol; 4-amino-2-(5-chloro-2-thienyl)-phenol; 4-amino-2-(5-formyl-2-thienyl)phenol; 4-amino-2-(5-methyl-2-thienyl)-phenol and 4-amino-2-(5-nitro-2-thienyl)phenol.

3. The p-aminophenol derivative compound as defined in claim 1, wherein R1 represents said hydrogen and/or at least one of said R2, said R3 and said R4 represents said hydrogen or said methyl group and/or said X represents said sulfur or said oxygen.

4. The p-aminophenol derivative compound as defined in claim 1 and selected from the group consisting of 4-amino-2-(2-thienyl)phenol, 4-amino-2-(3-methyl-2-thienyl) phenol and 4-amino-2-(5-methyl-2-thienyl) phenol.

5. A dye composition for oxidative dyeing of keratin fibers, said dye composition comprising at least one coupler compound and at least one developer compound, said at least one developer compound comprising at least one p-aminophenol derivative compound of formula (I), or a physiologically compatible water-soluble salt thereof,

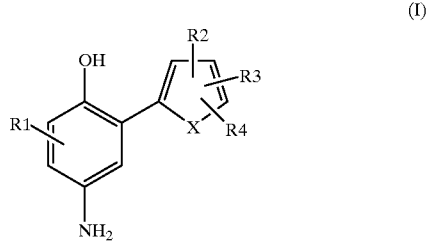

(I)

wherein X is oxygen, sulfur or NR5,

R$^1$ represents hydrogen, a halogen atom, a $C_1$- to $C_4$-alkyl group, a $C_1$- to $C_4$-hydroxyalkyl group or a $C_1$- to $C_4$-alkoxy group;

R2 and R4, independently of each other, each represent hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_6$-alkylamino group, a ($C_1$- to $C_6$)-dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR6 group, a —(CH$_2$)$_p$—CO$_2$R7 group or a —(CH$_2$)$_p$—R8 group, with p=1, 2, 3 or 4, a —C(R9)=NR10 group or a C(R11)H—NR12R13 group;

R3 represents -hydrogen, a halogen atom, a $C_1$- to $C_6$-alkyl group, or a —C(O)H group;

R5 represents hydrogen, a $C_1$- to $C_6$-alkyl group, a $C_1$- to $C_4$-hydroxyalkyl group, a phenyl group or an acetyl group;

R6 represents hydrogen, a hydroxy group, a nitro group, an amino group, a —CO$_2$R7 group or a —C(O)CH$_3$ group;

R7, R9 and R11 each represent, independently of each other, hydrogen or a $C_1$- to $C_4$-alkyl group;

R8 represents an amino group or a nitrile group;

R10, R12 and R13 each represent, independently of each other, hydrogen, a hydroxy group, a $C_1$- to $C_4$-alkyl group, a $C_1$- to $C_4$-hydroxyalkyl group, a 3- to $C_4$-dihydroxyalkyl group or a group of formula (II):

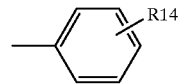

(II)

and R14 represents hydrogen, an amino group or a hydroxy group.

6. The dye composition as defined in claim 5, wherein said at least one p-aminophenol derivative compound of formula (I) is selected from the group consisting of 4-amino-2-(2-thienyl)-phenol; 4-amino-2-(2-furyl)-phenol; 4-amino-2-(pyrrol-2-yl)-phenol; 4-amino-2-(1-methyl-1H-pyrrol-2-yl)phenol; 4-amino-3-chloro-2-(2-thienyl)-phenol; 4-amino-3-methyl-2-(2-thienyl)-phenol; 4-amino-5-chloro-2-(2-thienyl)-phenol; 4-amino-5-methyl-2-(2-thienyl)-phenol; 4-amino-6-chloro-2-(2-thienyl)-phenol; 4-amino-6-methyl-2-(2-thienyl)-phenol; 4-amino-2-(3-acetyl-2-thienyl)-phenol; 4-amino-2-(3-chloro-2-thienyl)-phenol; 4-amino-2-(3-formyl-2-thienyl)-phenol; 4-amino-2(3-methyl-2-thienyl)-phenol; 4-amino-2-(3-nitro-2-thienyl)phenol; 4-amino-2-(4-acetyl-2-thienyl)-phenol; 4-amino-2-(4-chloro-2-thienyl)phenol; 4-amino-2-(4-formyl-2-thienyl)-phenol; 4-amino-2-(4-methyl-2-thienyl)phenol; 4-amino-2-(4-nitro-2-thienyl)phenol; 4-amino-2-(5-acetyl-2-thienyl)-phenol; 4-amino-2-(5-chloro-2-thienyl)-phenol; 4-amino-2-(5-formyl-2-thienyl)-phenol; 4-amino-2-(5-methyl-2-thienyl)-phenol and 4-amino-2-(5-nitro-2-thienyl)phenol.

7. The dye composition as defined in claim 5, wherein R1 represents said hydrogen and/or at least one of said R2, said R3 and said R4 represents said hydrogen or said methyl group and/or said X represents said sulfur or said oxygen.

8. The dye composition as defined in claim 5, wherein said at least one p-aminophenol derivative compound of formula (I) is selected from the group consisting of 4-amino-2-(2-thienyl)phenol, 4-amino-2-(3-methyl-2-thienyl)phenol and 4-amino-2-(5-methyl-2-thienyl)phenol.

9. The dye composition as defined in claim 5, wherein said at least one p-aminophenol derivative compound of formula (I) is present in an amount of 0.005 to 20.0 percent by weight.

10. The dye composition as defined in claim 5, wherein said at least one coupler compound is selected from the group consisting of 2,6-diaminopyridine, 2-amino-4-[(2-hydroxyethyl)-amino]anisole, 2,4-diamino-1-fluoro-5-methylbenzene, 2,4-diamino-1-methoxy-5-methylbenzene, 2,4-diamino-1-ethoxy-5methylbenzene, 2,4-diamino-1-(2-hydroxyethoxy)-5-methylbenzene, 2,4-di[(2-hydroxyethyl)-amino]-1,5-dimethoxy-benzene, 2,3-diamino-6-methoxypyridine, 3-amino-6-methoxy-2-(methylamino)-pyridine, 2,6-diamino-3,5-dimethoxy-pyridine, 3,5-diamino-2,6-dimethoxy-pyridine, 1,3-diaminobenzene, 2,4-diamino-1-(2-hydroxyethoxy)benzene, 2,4-diamino-1, 5-di (2-hydroxyethoxy)benzene, 1-(2-aminoethoxy)-2,4-diamino-benzene, 2-amino-1-(2-hydroxyethoxy)-4-methyl-aminobenzene, 2,4-diamino-phenoxyacetic acid, 3-[di(2-hydroxyethyl)amino]-aniline, 4-amino-2-di[(2-hydroxy-ethyl)amino]-1-ethoxybenzene, 5-methyl-2-(1-methylethyl) phenol, 3-[(2-hydroxy-ethyl)amino]aniline, 3-[(2-aminoethyl)amino]-aniline, 1,3-di(2,4-diaminophenoxy)-propane, di(2,4-diaminophenoxy)methane, 1,3-diamino-2, 4-dimethoxybenzene, 2,6-bis(2-hydroxyethyl)

aminotoluene, 4-hydroxyindole, 3-dimethylaminophenol, 3-diethylaminophenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)-amino]acetamide, 5-[(2-hydroxyethyl)-3-aminophenol, 2-[(3-hydroxyphenyl)-amino]acetamide, 5-[(2-hydroxyethyl)-amino]-2methylphenol, 3-[(2-hydroxyethyl)-amino]phenol, 3-[(2-methoxyethyl)-amino]phenol, 5-amino-2-ethylphenol, 2-(4-amino-2-hydroxyphenoxy)ethanol, 5-[(3-hydroxypropyl)amino]-2-methylphenol, 3-[(2, 3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylendioxyphenol, 3,4-methylendioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4-(2H)-benzoxazine, 6-amino-3,4-dihydroxy-1,4(2H)-benzoxazine, 3-methyl-1-phenyl-5-pyrazolone, 5,6-dihydroxyindole, 5,6-dihydroxyindolene, 5-hydroxyindole, 6-hydroxyindole, 7-hydroxyindole and 2,3-indolindione.

11. The dye composition as defined in claim 5, containing from 0.005 to 20 percent by weight of said at least one coupler compound and from 0.005 to 20 percent by weight of said at least one developer compound.

12. The dye composition as defined in claim 5, further comprising at least one direct dye compound.

13. The dye composition as defined in claim 12, wherein said at least one direct dye compound is selected from the group consisting of 6-amino-2-methylphenol, 2-amino-5-methylphenol, triphenylmethane dye compounds, aromatic nitro dye compounds, azo dye compounds, cationic dye compounds, dispersion dye compounds and cationic dye compounds.

14. The dye composition as defined in claim 5, further comprising water and having a pH from 6.5 to 11.5 and consisting of a hair dye composition.

15. A hair dye composition for oxidation dyeing of hair, said hair dye composition having a pH of from 6.5 to 11.5 and comprising water, from 0.5 to 30 percent by weight of at least one surfactant compound, 0.1 to 25 percent by weight of a thickener, from 0.1 to 5.0 percent by weight of a hair care substance, from 0.005 to 20 percent by weight of at least one coupler compound and from 0.005 to 20 percent by weight of at least one developer compound, wherein said at least one developer compound comprises at least one p-aminophenol derivative compound of formula (I), or a physiologically compatible water-soluble salt thereof,

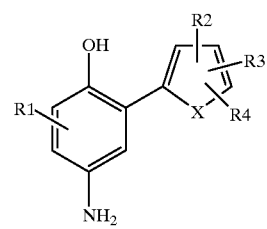

(I)

wherein X is oxygen, sulfur or NR5,
R1 represents hydrogen, a halogen atom, a $C_1$- to $C_4$-alkyl group, a $C_1$- to $C_4$-hydroxyalkyl group or a $C_1$- to $C_4$-alkoxy group;
R2 and R4, independently of each other, each represent hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_6$-alkylamino group, a ($C_1$- to $C_6$)-dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a $C_3$- to $C_4$-dihydroxyalkyl group, a —CH=CHR6 group, a —(CH$_2$)$_p$—CO$_2$R7 group or a —(CH$_2$)$_p$-R8 group, with p=1, 2, 3 or 4, a —C(R9)=NR10 group or a C(R11)H-NR12R13 group;
R3 represents hydrogen, a halogen atom, a $C_1$- to $C_6$-alkyl group, or a —C(O)H group;
R5 represents hydrogen, a $C_1$- to $C_6$-alkyl group, a $C_1$- to $C_4$-hydroxyalkyl group, a phenyl group or an acetyl group;
R6 represents hydrogen, a hydroxy group, a nitro group, an amino group, a —CO$_2$R7 group or a —C(O)CH$_3$ group;
R7, R9 and R11 each represent, independently of each other, hydrogen or a $C_1$- to $C_4$-alkyl group;
R8 represents an amino group or a nitrile group;
R10, R12 and R13 each represent, independently of each other, hydrogen, a hydroxy group, a $C_1$- to $C_4$-alkyl group, a $C_1$- to $C_4$-hydroxyalkyl group, a C3- to $C_4$-dihydroxyalkyl group or a group of formula (II):

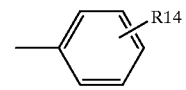

(II)

and R14 represents hydrogen, an amino group or a hydroxy group.

16. A method of dyeing hair, said method comprising the steps of:
a) mixing an oxidation dye composition with an oxidizing agent in a weight ratio of dye composition to oxidizing agent of 5:1 to 1:2 to form a ready-to-apply hair dyeing mixture;
b) applying the ready-to-apply hair dyeing mixture to the hair;
c) after the applying of step b), allowing the hair dyeing mixture to act on the hair for from about 10 to 45 minutes at 15 to 50° C.;

d) subsequently rinsing the hair with water and drying;
wherein said oxidation dye composition contains water, at least one coupler compound, at least one developer compound, wherein said at least one developer compound comprises at least one p-aminophenol derivative compound of formula (I), or a physiologically compatible water-soluble salt thereof,

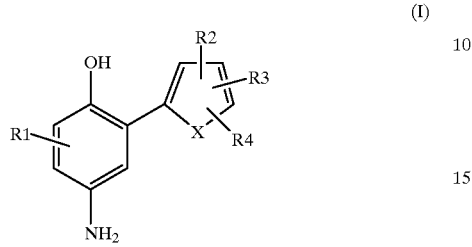

(I)

wherein X is oxygen, sulfur or NR5,

R1 represents hydrogen, a halogen atom, a $C_1$- to $C_4$-alkyl group, a $C_1$- to C4-hydroxyalkyl group or a $C_1$- to $C_4$-alkoxy group;

R2 and R4, independently of each other, each represent hydrogen, a hydroxy group, a halogen atom, a cyano group, a $C_1$- to $C_4$-alkoxy group, a $C_1$- to $C_6$-alkyl group, a $C_1$- to $C_4$-alkylthioether group, a mercapto group, a nitro group, an amino group, a $C_1$- to $C_6$-alkylamino group, a ($C_1$- to $C_6$)-dialkylamino group, a —C(O)H group, a —C(O)CH$_3$ group, a —C(O)CF$_3$ group, a —Si(CH$_3$)$_3$ group, a $C_1$- to $C_4$-hydroxyalkyl group, a C3- to $C_4$-dihydroxyalkyl group, a —CH=CHR6 group, a —(CH$_2$)$_p$—CO$_2$R7 group or a —(CH$_2$)$_p$—R8 group, with p=1, 2, 3 or 4, a —C(R9)=NR10 group or a C(R11)H-NR12R13 group;

R3 represents hydrogen, a halogen atom, a $C_1$- to $C_6$-alkyl group, or a —C(O)H group;

R5 represents hydrogen, a $C_1$- to $C_6$-alkyl group, a $C_1$- to $C_4$-hydroxyalkyl group, a phenyl group or an acetyl group;

R6 represents hydrogen, a hydroxy group, a nitro group, an amino group, a —CO$_2$R7 group or a —C(O)CH$_3$ group;

R7, R9 and R11 each represent, independently of each other, hydrogen or a $C_1$- to $C_4$-alkyl group;

R8 represents an amino group or a nitrile group;

R10, R12 and R13 each represent, independently of each other, hydrogen, a hydroxy group, a $C_1$- to $C_4$-alkyl group, a $C_1$- to $C_4$-hydroxyalkyl group, a C3- to $C_4$-dihydroxyalkyl group or a group of formula (II):

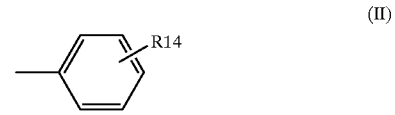

(II)

and R14 represents hydrogen, an amino group or a hydroxy group.

* * * * *